(12) United States Patent
Ziegler et al.

(10) Patent No.: US 6,228,839 B1
(45) Date of Patent: *May 8, 2001

(54) USE OF KERATINOCYTE GROWTH FACTOR TO IMPROVE OXIDATIVE STATUS

(75) Inventors: Thomas R. Ziegler, Lilburn; Dean P. Jones, Decatur, both of GA (US)

(73) Assignee: Emory University, Atlanta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/216,637

(22) Filed: Dec. 18, 1998

Related U.S. Application Data

(60) Provisional application No. 60/068,320, filed on Dec. 19, 1997, now abandoned.

(51) Int. Cl.[7] .................................................. A61K 38/18

(52) U.S. Cl. ............................................. 514/12; 514/21

(58) Field of Search .......................................... 514/12, 21

(56) References Cited

U.S. PATENT DOCUMENTS

| | | | |
|---|---|---|---|
| 5,607,975 | * 3/1997 | Smith et al. | 514/563 |
| 5,654,405 | 8/1997 | Rubin et al. | 530/387.9 |
| 5,665,870 | 9/1997 | Rubin et al. | 530/412 |
| 5,814,605 | 9/1998 | Pierce et al. | 514/12 |

FOREIGN PATENT DOCUMENTS 619 370 A1 * 10/1994 (EP) .

OTHER PUBLICATIONS

Aaronson and Todaro (1968) "SV40 T Antigen Induction and Transformation in Human Fibroblast Cell Strains" *Virology* 36:254–261.
Aw et al. (1992) "Absorption and Lymphatic Transport of Peroxidized Lipids By Rat Small Intestine In Vivo: Role of Mucosal GSH" *Am. J. Physiol.* 262:G99–G106.
Bai et al. (1996) "GSH Transport and GSH–Dependent Detoxication In Small Intestine of Rats Exposed In Vivo To Hypoxia" *Am. J. Physiol.* 271:G701–G706.
Burdon, Roy H. (1995) "Superoxide and Hydrogen Peroxide in Relation to Mammalian Cell Proliferation" *Free Radical Biology & Medicine* 18:775–794.
Burdon et al. (1994) "Endogenously Generated Active Oxygen Species and Cellular Glutathione Levels in Relation to BHK–21 Cell Proliferation" *Free Rad. Res.* 21:121–133.
Chen et al. (1988) "Effect Of Endotoxin On the Rat Colon Glutathione Level" *Biochemical and Biophysical Research Communications* 151:844–850.
Cho et al. (1981) "Tissue Glutathione as a Cyst(e)ine Reservoir During Fasting and Refeeding of Rats" *J. Nutr.* 111:914–922.
Cornell and Meister (1976) "Glutathione and γ–Glutamyl Cycle Enzymes in Crypt and Villus Tip Cells of Rat Jejunal Mucosa" *Proc. Natl. Acad. Sci.* 73:420–422.
Dahm and Jones (1994) "Secretion of Cysteine and Glutathione From Mucosa to Lumen in Rat Small Intestine" *Am. J. Physiol.* 267:G292–G300.
Darmon et al. (1993) "Oxidative Stress May Contribute to the Intestinal Dysfunction of Weanling Rats Fed a Low Protein Diet" *J. Nutr.* 123:1068–1075.
Farrell et al. (1998) "Keratinocyte Growth Factor Protects Mice From Chemotherapy and Radiation–Induced Gastrointestinal Injury and Mortality" *Cancer Research* 58:933–939.
Finch et al. (1989) "Human KGF Is FGF–Related With Properties of a Paracrine Effector of Epithelial Cell Growth" *Science* 245:752–755.
Frank et al. (1997) "The Human Homologue of a Bovine Non–Selenium Glutathione Peroxidase Is a Novel Keratinocyte Growth Factor–Regulated Gene" *Oncogene* 14:915–921.
Gilbert, H.F. (1989) "Thermodynamic and Kinetic Constraints On Thiol/Disulfide Exchange Involving Glutathione Redox Buffers" In: Glutathione Centennial. Molecular Perspectives and Clinical Implications, Edited by N. Taniguchi, T. Higashi, Y. Sakamoto, and A. Meister. Academic Press, San Diego, CA pp. 73–87.
Hagemann and Stragand (1977) "Fasting and Refeeding: Cell Kinetic Response of Jejunum, Ileum and Colon" *Cell Tissue Kinet.* 10:3–14.
Hagen et al. (1990) "Fate of Dietary Glutathione: Disposition in the Gastrointestinal Tract" *Am. J. Physiol.* 259:G530–G535.
Housley et al. (1994) "Keratinocyte Growth Factor Induces Proliferation of Hepatocytes and Epithelial Cells Throughout the Rat Gastrointestinal Tract" *J. Clin. Invest.* 94:1764–1777.
Hwang and Sinskey (1991) "The Role of Oxidation–Reduction Potential in Monitoring Growth of Cultured Mammalian Cells" Butterworth–Heinemann Ltd., Jordan Hill, Oxford, pp. 548–568.
Jahoor et al. (1995) "Protein–Deficient Pigs Cannot Maintain Reduced Glutathione Homeostasis When Subjected to the Stress of Inflammation" *J. Nutr.* 125:1462–1472.

(List continued on next page.)

*Primary Examiner*—M. Moezie
(74) *Attorney, Agent, or Firm*—Greenlee, Winner and Sullivan, P.C.

(57) ABSTRACT

The present disclosure provides methods for minimizing oxidative damage in an animal or human during or after malnutrition, underfeeding or fasting, especially during refeeding after undernutrition or malnutrition, and for minimizing oxidant damage during or after toxicity resulting from chemotherapy, alcoholism, irradiation therapy or chemical or environmental exposure. The present methods comprise the step of administering an amount of keratinocyte growth factor effective for improving gut and/or systemic antioxidant status.

7 Claims, 4 Drawing Sheets

OTHER PUBLICATIONS

Jonas et al. (1998) "Keratinocyte Growth Factor (KGF) Improves Colonic Glutathione Redox State In Rats During Fasting" Abstract. Experimental Biology '99.

Kawamura et al. (1994) "Enhancement by Tocoretinate of Epidermal Growth Factor–Induced DNA Synthesis in Human Intestinal Epithelial Cells" *Digestive Diseases and Sciences* 39:2191–2196.

Kelly, Frank J. (1993) "Glutathione Content of the Small Intestine: Regulation and Function" *British Journal of Nutrition* 69:589–596.

Lash et al. (1986) "Exogenous Glutathione Protects Intestinal Epithelial Cells From Oxidative Injury" *Proc. Natl. Acad. Sci.* 83:4641–4645.

Martensson et al. (1990) "Glutathione Is Required For Intestinal Function" *Proc. Natl. Acad. Sci.* 87:1715–1719.

McKenzie et al. (1996) "Evidence of Oxidant–Induced Injury to Epithelial Cells During Inflammatory Bowel Disease" *J. Clin. Invest.* 98:136–141.

Ogasaware et al. (1989) "Glutathione and Its Related Enzymes in the Small Intestinal Mucosa of Rats: Effects of Starvation and Diet" *Res. Exp. Med.* 189:195–204.

Pelissier et al. (1993) "Effects of Protein Deficiency On Lipid Peroxidation In the Small Intestine and Liver of Rats" *Fd. Chem. Toxic.* 31:59–62.

Robinson et al. (1997) "Starvation Enhances Hepatic Free Radical Release Following Endotoxemia" *Journal of Surgical Research* 69:325–330.

Samiec et al. (1998) "Glutathione In Human Plasma: Decline In Association With Aging, Age–Related Macular Degeneration, and Diabetes" *Free Radical Biology & Medicine* 24:699–704.

Steiner et al. (1968) "Effect of Starvation On the Tissue Composition of the Small Intestine In the Rat" *American Journal of Physiology* 215:75–77.

Sundaresan et al. (1995) "Requirement for Generation of $H_2O_2$ for Platelet–Derived Growth Factor Signal Transduction" *Science* 270:296–299.

Zeeh et al. (1996) "Keratinocyte Growth Factor Ameliorates Mucosal Injury In an Experimental Model of Colitis in Rats" *Gastroenterology* 110:1077–1083.

Ziegler, T.R. (1996) "Molecular Mechanisms of Intestinal Injury, Repair and Growth" In Gut Dysfunction in Critical Illness. Rombeau, J.L. and Takala, J. (eds.) Springer–Verlag, New York, pp. 25–52.

Ziegler, et al. (1995) "A Comparison of Rat Small Intestinal Insulin and Insulin–Like Growth Factor I Receptors During Fasting and Refeeding" *Endocrinology* 136:5148–5154.

Ziegler, et al. (1985) "Role of Reversible Oxidation–Reduction of Enzyme Thiols–Disulfides In Metabolic Regulation" *Ann. Rev. Biochem.* 54:305–329.

* cited by examiner

USE OF KERATINOCYTE GROWTH FACTOR TO IMPROVE OXIDATIVE STATUS

CROSS REFERENCE TO RELATED APPLICATIONS

This application claims priority from U.S. Provisional Patent Application 60/068,320, filed Dec. 19, 1997 now abandoned.

ACKNOWLEDGEMENT OF FEDERAL RESEARCH SUPPORT

The present invention was made, at least in part, with funding from the National Institutes of Health. Accordingly, the United States Government has certain rights in this invention.

BACKGROUND OF THE INVENTION

Growth of the gastrointestinal mucosa is markedly influenced by nutritional status and enteral nutrient availability. This is evidenced by the disproportionate loss of gut mucosal mass relative to body weight during starvation and other states of malnutrition [Steiner et al. (1968) Am. J. Physiol. 215:75–77; Ziegler et al. (1995) Endocrinology 136:5148–5154]. Fasting or severe protein-calorie restriction result in mucosal cell atrophy, decreased digestive enzyme activity and absorptive capacity, and impaired intestinal barrier function [Ziegler, T. R. (1996) Springer-Verlag, New York, pp. 25–52; Hagemann and Stragand (1977) Cell Tiss. Kinet. 10:3–14]. Malnutrition is also associated with reduced antioxidant capacity in the intestinal mucosa [Ogasawara et al. (1989) Res. Exp. Med. 189:195–204]. Enteral refeeding after a period of malnutrition rapidly regenerates intestinal cellularity and mucosal mass [Ziegler, T. R. (1996) Springer-Verlag, New York, pp. 25–52; Hagemann and Stragand (1977) Cell Tiss. Kinet. 10:3–14; Ogasawara et al. (1989) Res. Exp. Med. 189:195–204].

The tripeptide glutathione (L-glutamyl-L-cysteinyl-glycine, GSH) is the most abundant low molecular weight thiol in mammalian cells and plays a key role in the detoxification of cellular free radicals, chemical toxins, and carcinogens [Robinson et al. (1997) J. Surg. Res. 69:325–330]. GSH deactivates potentially harmful oxidants by serving as a hydrogen donor to reduce reactive molecules with concomitant conversion to its oxidized disulfide form, GSSG [Meister, A. (1991) Pharmacol. Ther. 51:155–194]. GSH is synthesized endogenously in mucosal cells utilizing specific amino acid substrates, can be derived exogenously from dietary sources, or may enter the gut lumen via bile and by direct secretion from mucosal cells [Hagen et al. (1990) Am J. Physiol. 259:G530–G535; Dahm and Jones (1994) Am. J. Physiol. 267:G292–G300]. GSH present in the gut lumen and within enterocytes appears to be required for normal intestinal function, in part, by protecting intestinal epithelial cells from damage by dietary electrophiles and fatty acid hydroperoxides [Lash et al. (1986) Proc. Natl. Acad. Sci. 83:4641–4645; Martensson et al. (1989) Proc. Natl. Acad. Sci. 87:1715–1719; Aw et al. (1992) Am. J. Physiol. 262:G99–G106]. GSH also appears to play a role in maintaining the proper sulfhydryl/disulfide balance of gut luminal proteins, potentially modulating activity of thiol-containing enzymes on the brush border [Gilbert, H. F. (1989) Academic, San Diego, pp. 73–87; Ziegler, D. M. (1985) Annu. Rev. Biochem. 54:305–329].

Previous studies demonstrate that malnutrition reduces tissue GSH content [Ogasawara et al. (1989) Res. Exp. Med. 189:195–204; Cho et al. (1981) J. Nutr. 111:914–922; Robinson et al. (1997) J. Surg. Res. 69:325–330]. In animal models, fasting or an insufficient dietary supply of amino acids that may serve as GSH substrates (e.g., glutamine and cysteine) depletes GSH levels in both small intestine and colon [Ogasawara et al. (1989) Res. Exp. Med. 189:195–204; Robinson et al. (1997) J. Surg. Res. 69:325–330; Kelly, F. J. (1993) Br. J. Nutr. 69:589–596]. Therefore, malnutrition-associated depletion of cellular GSH in gut epithelial cells may increase their susceptibility to oxidative injury and exacerbate the degeneration of the intestinal mucosa [Kelly, F. J. (1993) Br. J. Nutr. 69:589–596]. Also, there is evidence to suggest that GSH is involved in regulation of cell growth [Hwang and Sinskey (1991) Butterworth-Heinemann Ltd., Jordan Hill, Oxford, pp. 548–569].

In studies using a variety of cultured mammalian cells, a more reduced state of the extracellular GSH pool was associated with increased cell proliferation, while a more oxidized GSH pool was associated with slower cell growth [Hwang and Sinskey (1991) Butterworth-Heinemann Ltd., Jordan Hill, Oxford, pp. 548–569]. Intracellular and extracellular antioxidant status also appears to influence cell proliferation mediated by specific growth factor peptides, including platelet-derived growth factor (PDGF) and epidermal growth factor (EGF) [Sundaresan et al. (1995) Science 270:296–299; Burdon et al. (1994) Free Radical Res. 21:121–123; Burdon, R. (1995) Free Radical Biol. Med. 18:775–794; Kawamura et al. (1994) Dig. Dis. Sci. 39:2191–2196]. It is therefore possible that the reducing environment regulated by GSH in gut mucosa may be important not only for detoxification reactions allowing normal tissue growth and function, but also for regulating cell proliferation in response to nutrients and growth factors.

Keratinocyte growth factor (KGF), a member of the fibroblast growth factor (FGF) family, is a mesenchymally-derived peptide which appears to be an important endogenous mediator of epithelial growth, regeneration and repair [Finch et al. (1989) Science 245:752–755]. Exogenous administration of recombinant human KGF in cell culture systems or in in vivo animal models stimulates proliferation and differentiation of specific epithelial cell types, including hepatocytes and enterocytes, and also appears to have cytoprotective functions [Aukerman et al. (1997) Springer-Verlag, New York, pp. 293–303]. In healthy rats fed ad libitum diets, administration of KGF induced epithelial cell proliferation in the stomach, duodenum, colon, liver and pancreas [Housley et al. (1994) J. Clin. Invest. 94:1764–1777].

We recently found that the administration of KGF enhances small intestinal and colonic mucosal growth during enteral refeeding after a 3-day period of fasting. The mechanisms by which KGF acts as a potent gut mitogen during enteral nutrition are unclear. The current study was designed to investigate mucosal GSH status associated with gut growth stimulated by enteral nutrition and by KGF in a fasting/refeeding rat model. The major aims of this study were: 1) to determine whether different levels of enteral refeeding changes small intestinal and colonic mucosal levels of GSH and GSSG and the GSH redox potential; and 2) to assess the effects of the gut-trophic hormone KGF on mucosal GSH antioxidant capacity in models of altered enteral nutrition. A further aim was to determine whether changes in mucosal GSH status are associated with changes in indices of mucosal growth.

There is a strong need for methods for treating patients and animals suffering from malnutrition, starvation and/or malabsorption, especially during refeeding after a period of insufficient nutrition, and there is also a longfelt need in the art for methods of treatment which result in an improvement in local and/or systemic improvement in the oxidation state, particularly as measured by the glutathione/reduced glutathione ratio, due to age, disease, catabolic stress, sequelae to certain medical treatment regimens, trauma, inflammation, among other conditions. The present invention meets that need.

SUMMARY OF THE INVENTION

The present invention provides a method for the improvement of systemic oxidation-reduction state, as measured in the study described hereinbelow by the GSH and GSSG concentrations and the GSH reducing potential, as well as an improvement of the oxidation-reduction state of the gastrointestinal epithelial cells, for example, during refeeding after fasting, malnutrition or other stress. Administration of KGF to a human or animal during fasting, malnutrition, a course of chemotherapy or irradiation therapy, or other stress improves systemic antioxidant strains and serves to reduce or prevent oxidative stress or damage in the gastrointestinal tract. The present method includes the step of administering an amount of keratinocyte growth factor effective to improve antioxidant status by a suitable means. Desirably, the keratinocyte growth factor corresponds in amino acid sequence to that of the animal or human to whom it is administered. Suitable routes of administration include, but are not limited to, parenteral, nonparenteral, intraperitoneal and intravenous.

The present invention further provides methods for the treatment of medical (or veterinary) conditions so as to improve the general, tissue and systemic antioxidant oxidation status, the conditions including, but not limited to, aging, general malnutrition associated with aging, disease, malabsorption disorders or psychological dysfunction, inflammatory bowel disease, chemotherapy, radiation exposure or therapy, corticosteroid therapy, toxin ingestion, alcoholism and inflammation associated with burns, sepsis, infection or trauma. The oxidation-reduction status can be measured as specifically exemplified herein, by GSH and GSSH concentrations and the calculated GSH redox state ratio in plasma or in a tissue sample of a patient or animal.

DETAILED DESCRIPTION OF THE INVENTION

Figure 1:
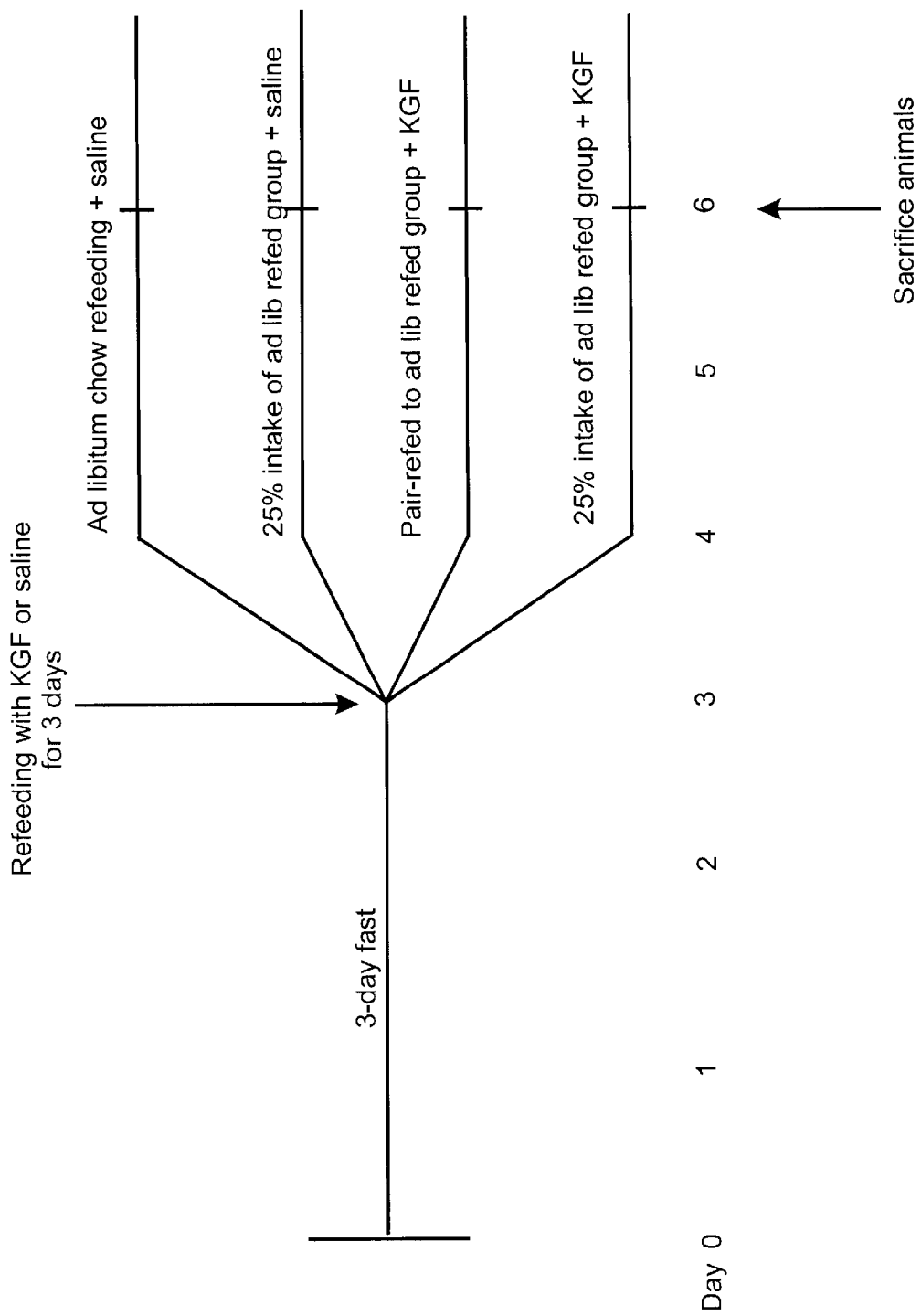
FIG. 1 presents the study design overview for the study of redox state and KGF administration.

As used herein, keratinocyte growth factor (KGF) is a growth factor which stimulates cell growth and division of cells containing the cognate cell surface receptor (epithelial cells). The amino acid sequence of human KGF and the nucleotide sequence encoding it, as are methods for recombinant production of same, are given in EP 619,271 [published Oct. 12, 1994], incorporated by reference herein in its entirety. A coding and amino acid sequence are also given in U.S. Pat. No. 5,665,870 [Rubin et al., Sep. 9, 1997], incorporated by reference herein in its entirety. KGF is a member of the fibroblast growth factor family. It acts selectively on epithelial cells, and it is especially active in keratinocytes. See U.S. Pat. No. 5,665,870 [supra] for a discussion of the purification of recombinant KGF. Purification of nonrecombinant KGF from M426 human embryonic fibroblasts has been described in Aaronson and Todaro [(1968) Virology 36:254–261].

For use in the methods of the present invention, KGF can be administered subcutaneously, intravenously or enterally, with formulation with pharmaceutically carriers appropriate for the route of administration, as obvious to one of ordinary skill in the art. EP 619,370 [supra] provides discussion and guidance for the formulation of pharmaceutical compositions containing KGF as an active ingredient as well as methods for bioassay of KGF, and those teachings are specifically incorporated by reference herein. Desirably, the KGF preparation in the pharmaceutical preparation is more than 25%, preferably more than 50%, biologically active. Dosage ranges for administration to a human or animal include, but are not limited to, from about 0.01 to about 10 mg/kg body weight, or from 0.1 to about 7.5 mg/kg or from about 1 to about 5 mg/kg.

The different levels of refeeding and/or KGF significantly regulated mucosal growth indices in the jejunum, ileum and colon. In saline-treated rats, underfeeding caused a statistically significant 22 percent reduction in jejunal and a 17 percent reduction in ileal total mucosal height values (NS). Post-fast underfeeding also significantly reduced jejunal and ileal crypt depth by 54 percent and did not significantly alter colonic crypt depth. KGF treatment did not affect jejunal mucosal growth indices, but significantly increased ileal total mucosal height and crypt depth during underfeeding. KGF significantly increased colonic crypt depth in both ad libitum-refed and 25% refed rats, by 47 and 25 percent, respectively.

GSH and GSSG levels in jejunal, ileal and colonic mucosa are shown in Table 1. There was no significant main effect of diet on jejunal GSH or GSSG levels by two-factor ANOVA, but a significant main effect of treatment (KGF versus saline) on both GSH and GSSH in this tissue (P=0.006, GSSG P=0.032). Underfeeding after the 3-day fast significantly reduced jejunal GSH levels in animals receiving saline. KGF administration in the 25% refed animals significantly increased GSH levels and tended to increase levels in ad libitum refed rats (NS). In malnourished animals, GSH levels rose from 4.46±0.8 to 6.93±0.44 nmol/mg protein with KGF treatment (P<0.01), a value that was indistinguishable from ad libitum-refed rats. Jejunal levels of GSSG, the oxidized form of GSH, were lower in both KGF-treated groups relative to their respective saline-treated controls given similar diets, but values between groups were not significantly different (Table 1).

Figure 2A:
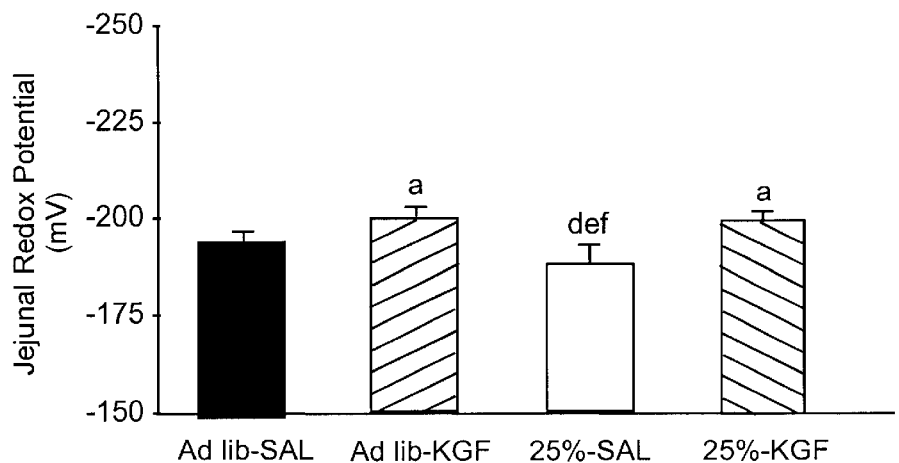
FIGS. 2A–2C illustrate the mucosal redox potential ($E_h$) values in jejunum (FIG. 2A), ileum (FIG. 2B) and colon (FIG. 2C) from rats fed ad libitum or at 25% of ad libitum after a 3-day fast with or without KGF administration. $E_h$ values are expressed in mV and calculated using mucosal concentrations of GSH and GSSG as described hereinbelow. [a]P<0.05 versus ad libitum-saline (Ad lib-SAL), [d]P<0.01 versus Ad libSAL; [e]P<0.01 versus ad libitum-KGF (Ad lib-KGF); [f]P<0.01 versus 25% refed-KGF (25% KGF).

Data on jejunal GSH redox potential ($E_h$) are shown in FIG. 2A. $E_h$ reflects the redox state of the mucosal GSH- GSSG pool and thus, the local reducing capacity of GSH. There was no significant main effect of diet on $E_h$ by 2-factor ANOVA, but a marked effect of KGF administration was observed (P=0.001, treatment main effect). $E_h$ values were significantly less negative in the 25%-SAL group (−186±3 mV) compared to the A-SAL (−195±2 mV) and A-KGF (−201±1 mV) groups, indicating that the decreased level of refeeding resulted in a more oxidized jejunal mucosal GSH pool. KGF treatment slightly reduced $E_h$ in ad libitum-refed rats (P<0.005), but had the most significant effect in preventing GSH oxidation in the jejunal mucosal in the underfed rats (P<0.01). This is evidenced by $E_h$ values in the 25%-KGF group (−202±2, FIG. 2A) increasing to those seen in ad libitum fed animals.

The main effects of diet and treatment on ileal GSH levels were not significant, but a marked interaction between these factors was observed (P=0.006). This response in reflected in the group mean data shown in Table 1. Values for ileal GSH significantly decreased by 38 percent during underfeeding. KGF treatment in 25%-refed animals markedly increased ileal GSH to values higher than in the other three groups. Mucosal GSSG in ileum was significantly affected by both diet and KGF treatment (P=0.037 and P=0.001, two-factor ANOVA). GSSG values fell approximately 2.25-fold when KGF was administered to either ad-libitum refed or 25%-refed rats.

Figure 2B:
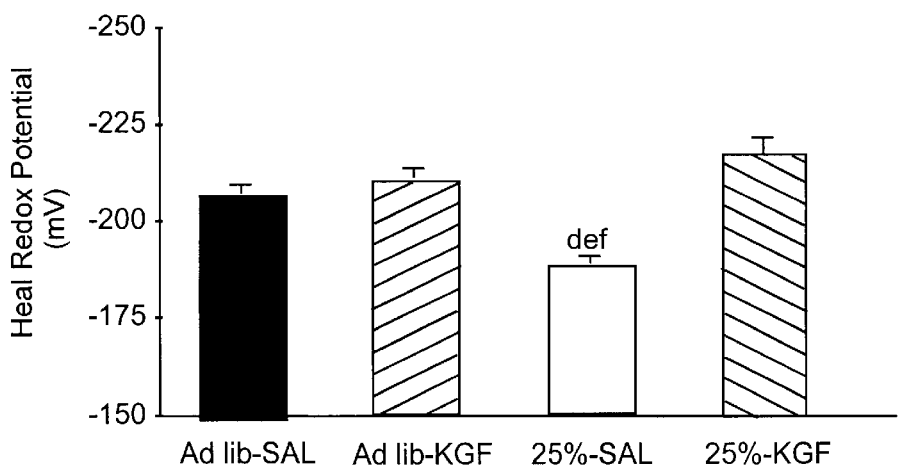

GSH redox potential in ileal mucosa was significantly altered by KGF treatment (P=0.003, two factor ANOVA), and a significant interaction between diet and KGF on $E_h$ was observed (P 0.001). As shown in FIG. 2B, E values in the 25% refed saline-treated rats were significantly less negative, or more oxidized, than in all other groups. KGF had no significant effect on ileal $E_h$ in ad libitum refed rats, but markedly reduced this index in undernourished refed animals from 186±6 mV (25%-SAL) to <215±4 (25%-KGF) (P<0.01).

Diet and KGF significantly regulated GSH levels in colonic mucosa (P=0.037 and P=0.019, respectively, 2-factor ANOVA) (Table 1). Post-fast underfeeding decreased GSH levels by 57 percent (P<0.05). Similar to the small intestine, KGF treatment increased colonic mucosal GSH and this response was influenced by the level of refeeding. KGF administration during ad libitum refeeding resulted in a modest 33 percent increase in GSH (NS), but with 25% refeeding KGF treatment resulted in a more than 2-fold increase in colonic mucosal GSH levels, to 25.8±3 nmol/mg protein (P<0.05).

Colonic GSSG was unaffected by diet but was significantly altered by KGF (P=0.026; 2 factor ANOVA). A significant interaction between diet and KGF administration was observed (P=0.022). In ad libitum-refed rats, KGF administration significantly decreased GSSG levels, suggesting that a lower proportion of the GSH pool was oxidized. Underfeeding decreased colonic GSSG values by 40 percent compared to ad libitum refed animals, but the effect of malnutrition was not observed in KGF-treated rats, indicative of the interaction between diet and KGF.

Figure 2C:
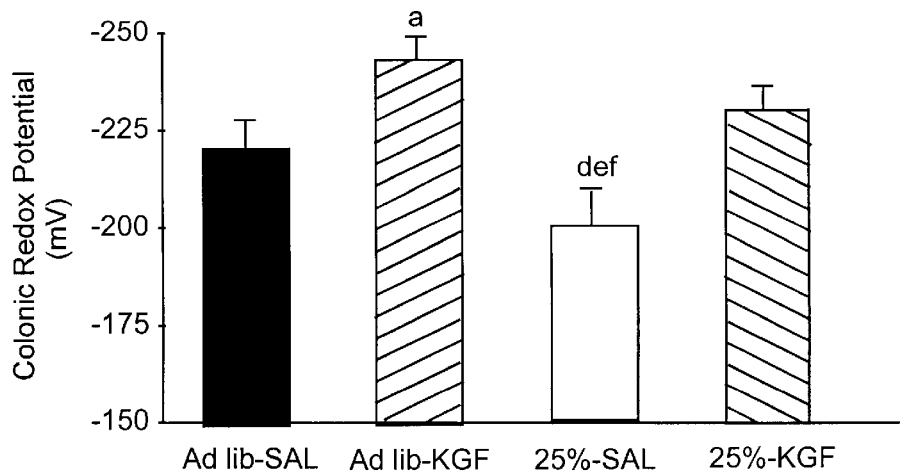
Figure 3A:
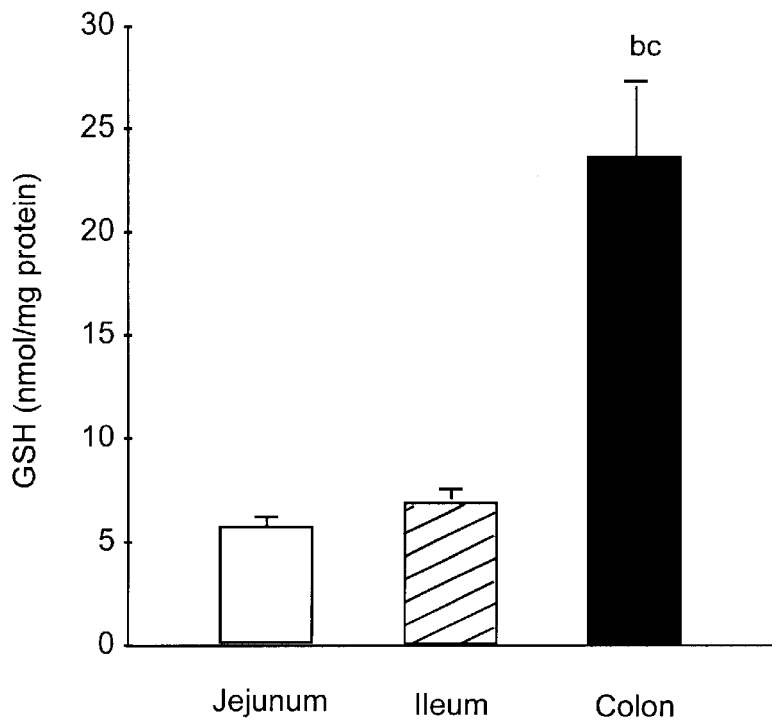
FIGS. 3A–3B graphically illustrate the proximal to distal intestinal gradient for GSH concentration (FIG. 3A) and GSH mucosal redox potential (FIG. 3B) in jejunum, ileum and colon of ad libitum-fed saline-treated rats. Redox potential values are expressed in mV and calculated using mucosal concentrations of GSH and GSSG as described in hereinbelow. [a]P<0.05 versus jejunum; [b]P<0.01 versus jejunum; P<0.01 versus ileum.
Figure 3B:
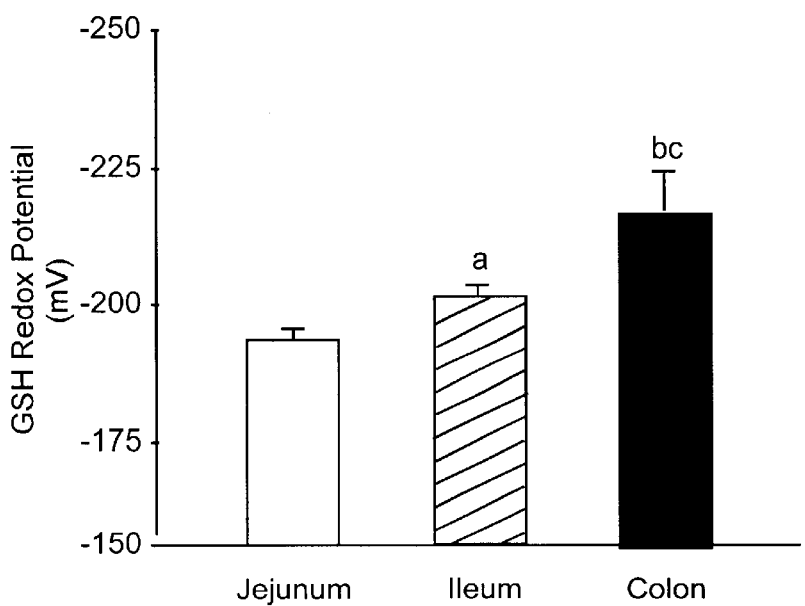

The redox potential of the colonic mucosal GSH pool was influenced by the level of refeeding (P=0.016, diet main effect) and KGF administration (P=0.001, treatment main effect). As shown in FIG. 2C, colonic redox potential was oxidized by 15 mV in the 25%-SAL group relative to the A-SAL group (P<0.01). KGF restored the colonic mucosal $E_h$ to a more reduced state during both ad libitum refeeding (to −243 mV; P<0.05) and 25% refeeding (to −231 mV; P<0.01).

With respect to the relationship between mucosal cellularity and GSH redox state, there was no significant relationship between GSH status and crypt depth or total mucosal height in jejunum. There were two marginally significant covariate effects between mucosal crypt depth and mucosal GSH level in the ileum (P=0.062) and also in the colon (P=0.078). In colon, the ANOVA results were similar to the ANOVA results, as KGF treatment was related to crypt depth regardless of GSH level. This suggests that after adjusting for effects of diet and GSH levels, there is a significant KGF effect to increase colonic crypt depth.

Regarding ileal crypt depth, the ANCOVA results were not the same as the ANOVA results. In the ANOVA, there was a significant 2-way interaction between KGF and diet effects. Thus, ileal crypt depth was markedly decreased by underfeeding in the saline-treated but not in the KGF-treated groups. After adjusting for effect of GSH, the decrease in ileal crypt depth with 25% refeeding was of similar magnitude in saline-treated and KGF-treated groups, implying that KGF increased ileal crypt depth, in part, by a GSH-dependent mechanism. In saline-treated animals, colon crypt depth was marginally associated with $E_h$ (P=0.092). However, in both saline treated and KGF-treated rats, colon crypt depth was significantly associated with mucosal GSH concentrations (P=0.006 and P=0.049, respectively).

FIGS. 2A–2C compare values for GSH and GSH redox potential ($E_h$) in jejunum, ileum and colon for the A-SAL group, demonstrating a marked proximal to distal intestinal gradient for these parameters. Values for GSH were similar in jejunum and ileum, but colonic levels were 3.25 to 4-fold greater than in small intestine in this model of refeeding (P<0.01, one-way ANOVA; FIG. 2A). Although GSH levels between jejunum and ileum were not significantly different, values for $E_h$ were modestly, but significantly reduced in the ileum compared to the jejunum (P<0.05) and further reduced in colon (P<0.01 versus both small bowel segments; FIG. 2B). Malnutrition induced a marked decrease in gut mucosal GSH levels, but the proximal to distal gut gradient for GSH and $E_h$ in the 25%-SAL group was similar to that observed the ad libitum-refed controls (Table 1). Similarly, KGF treatment in the setting of undernutrition did not alter the intestinal gradient of mucosal antioxidant capacity (Table 1).

To our knowledge, the current study is the first demonstration of growth-factor-induced regulation of tissue antioxidant status in vivo. Administration of the recombinant peptide KGF enhanced GSH levels and the GSH antioxidant capacity ($E_h$) in all portions of the bowel during limited enteral nutrient intake after a prolonged fast. GSH content in distal bowel regions (ileum and colon) were the most responsive to KGF, increasing by more than two-fold compared to the 25% refed rats. The malnutrition-induced oxidation of the GSH pool was completely prevented by KGF administration. KGF also significantly increased GSH redox potential in the jejunum and colon of ad libitum-refed rats. Based on these findings, therapeutic administration of KGF represents an effective method to prevent or treat oxidative injury of the gut mucosa during malnutrition and other causes or states of oxidative stress in the gut.

This study confirms and extends previous observations on malnutrition-associated GSH depletion in the intestine and other tissues such as liver [Ogasawara et al. (1989) *Res. Exp. Med.* 189:195–204; Cho et al. (1981) *J. Nutr.* 111:914–922; Kelly, F. J. (1993) *Br. J. Nutr.* 69:589–596]. This is the first study of gut mucosal GSH levels with fasting followed by different levels of enteral refeeding and represents the initial evaluation of the reducing potential of tissue GSH pools in response to altered nutrition. The degree of malnutrition induced by the 25% refeeding diet significantly depleted mucosal GSH levels throughout the intestine. Similarly, in this model, underfeeding resulted in substantial oxidation of the mucosal GSH pool in jejunum, and especially in ileum and in colon, as demonstrated by the less negative $E_h$ values.

The degree of gut mucosal atrophy or injury resulting from malnutrition is influenced by local antioxidant defenses, especially mucosal concentrations of GSH, the major intracellular thiol antioxidant [Kelly, F. J. (1993) Br. J. Nutr. 69:589–596, Bai et al. (1996) Am. J. Physiol. 271:G701–706; Meister and Meister (1976) Proc. Natl. Acad. Sci. 78:420–422]. As suggested in previous studies [Hwang and Sinskey (1991) Butterworth-Heinemann Ltd., Jordan Hill, Oxford, pp. 548–569], and by the data reported here, tissue GSH may affect the proliferative responses of epithelial cells to nutrients and growth factors. We explored this relationship using analysis of covariance methods because both the level of refeeding and KGF administration influenced redox and mucosal growth indices. Our data support the concept that the increase in ileal crypt depth induced by KGF is mediated, at least in part, by a GSH-dependent mechanism in the setting of undernutrition or malnutrition. In both saline treated and KGF-treated rats, colon crypt depth was significantly correlated with mucosal GSH concentrations. Taken together, these observations show that the level of GSH independently regulates an index of mucosal growth (crypt depth) in ileum and colon. Alternatively, changes in gut mucosal growth may influence gut mucosal GSH status.

Starvation for periods of 24 to 48 hours decreased GSH content in rat small intestine by 40 to 70% [Ogasawara et al. (1989) Res. Exp. Med. 189:195–204; Kelly, F. J. (1993) Br. J. Nutr. 69:589–596]. Protein deficiency also depresses GSH synthesis in various tissues [Jahor et al. (1995) J. Nutr. 125:1462–1472]. In one study, intestinal GSH levels were restored to the normal range within 24 hours of ad libitum enteral refeeding after a 48 hour fast [Ogasawara et al. (1989) Res. Exp. Med. 189:195–204]. We found that refeeding a protein-energy restricted diet resulted in significantly decreased mucosal GSH content in jejunum, ileum and colon by 28 to 60 percent as compared to ad libitum refeeding. The decrease in GSH with undernutrition was associated with a concomitant decrease in mucosal GSSG, the oxidized form of GSH, in the jejunum and colon. This alteration reflects the overall decrease in the content of the mucosal GSH pool in these tissues. In contrast, ileal mucosal GSSG levels increased by 55 percent in 25%-SAL group versus the A-SAL group, indicating that malnutrition regulates ileal GSH and GSSG content differently.

This is believed to be the first report that malnutrition impairs the reducing capacity of GSH in the intestinal mucosa. In all tissues studied, the functional measure of gut GSH antioxidant status, $E_h$ was markedly and significantly oxidized by the lower level of refeeding. Differences in mucosal $E_h$ values of from 15 to 39 mV were detected between treatment groups. This magnitude of change in the GSH redox potential has been reported in humans during physiological processes where serum antioxidants are depleted and increased reactive oxygen species are implicated in tissue damage [Samiec et al. (in press) Free Radical Biol.]. Changes in $E_h$ values in the range of 40 to 50 mV in human plasma result as a function of aging, chronic pulmonary disease, age-related macular degeneration and diabetes mellitus [Samiec et al. (in press) supra].

GSH is an important defense against toxins and reactive oxygen species in the intestinal mucosa, where a loss in GSH reducing capacity increases the susceptibility of the intestinal mucosa to injury. For example, enterocytes isolated from gut mucosal tissue of malnourished animals had severely decreased GSH concentrations, and upon exposure to a potent oxidant, hydrogen peroxide, were less viable and showed further cellular GSH depletion [Kelly, F. J. (1993) Br. J. Nutr. 69:589–596]. When GSH deficiency was induced in rats by administration of the specific GSH synthesis inhibitor buthionine sulfoxide (BSO), intestinal epithelial damage occurred throughout the intestine as evidenced by reduced height of intestinal mucosa, microvillus desquamation, and intracellular mitochondrial degeneration [Martensson et al. (1989) Proc. Natl. Acad. Sci. 87:1715–1719]. There are data to support the concept that free radicals are generated locally during malnutrition to induce oxidative stress in the gut mucosa. In animal studies, starvation and chronic protein-deficient feeding increased lipid peroxide concentrations and concomitantly decreased GSH concentrations in the small intestine [Pelissier et al. (1993) Food Chem. Toxicol. 31:59–62; Darmon et al. (1993) J. Nutr. 123:1068–1075]. Taken together with the available published literature, our study demonstrates that enteral nutrient availability is an important determinant of gut GSH antioxidant status. In the context of the present disclosure, improved antioxidant status means an increase in the ratio of reduced glutathione to oxidized glutathione. Improvement in antioxident status also encompasses an increase in the amount of reduced glutathione, especially in the gastrointestinal tract.

Our data demonstrate that administration of recombinant KGF prevented malnutrition-associated oxidation of the GSH pool. KGF and its specific tyrosine kinase receptor (KGF-R) are widely distributed in epithelial organs with mesenchymal components, such as skin, lung and the gastrointestinal tract [Finch et al. (1989) Science 245:752–755; Aukerman et al. (1997) Springer-Verlag, New York, pp. 293–303]. KGF administration in rodents decreases gut mucosal injury in experimental colitis [Zeeh et al. (1996) Gastroenterology 110:1077–1083], acetic-acid-induced gastric injury [Farrell et al. (in press) Cancer Res. 1998] and following chemotherapy and radiation [McKenzie et al. (1996) J. Clin. Invest. 98:136–141]. Mucosal inflammation is associated with increased oxidant-induced damage to epithelial cells [McKenzie et al. (1996) supra]. Without wishing to be bound by any particular theory, it is believed that a mechanism of KGF trophic action is to provide critical protection of the mucosa from toxins or reactive oxygen species. Although KGF did not significantly increase GSH levels in adequately refed animals, the reducing capacity of the GSH pool ($E_h$) was significantly improved by KGF in the jejunum and colon in these rat models. The reducing capacity, $E_h$, is a more sensitive measure of tissue GSH responses.

Our data establish the link between exogenous KGF administration and gut antioxidant capacity in vivo; however, it is possible that other growth factors have a similar effect on the GSH system. KGF is believed to exert specific effects on aspects of GSH antioxidant functions. In a recent in vitro study, KGF treatment of keratinocytes increased expression of the bovine non-selenium dependent glutathione peroxidase mRNA, suggesting a possible role for KGF in regulation of GSH-related enzymes [Frank et al. (1997) Oncogene 14:915–921]. Additional studies are required to determine whether changes in the expression of the genes encoding the GSH enzyme system or in enzyme activity are mechanistically related to the specific KGF action on the GSH/GSSG ratios in these models.

The underlying mechanism(s) responsible for changes in GSH status in response to diet or KGF were not examined in this study. Oxidation of GSH to GSSG can occur nonenzymatically or by association with specific enzymes, including glutathione-s-transferase (GST) and glutathione peroxidase (GSH-Px) [Meister, A. (1991) *Pharmacol. Ther.* 51:155–194]. The fall in mucosal GSH pools with underfeeding and the increase with KGF administration could involve several mechanisms, including alterations in GSH-metabolizing enzymes which regulate GSH breakdown and synthesis, and/or altered GSH utilization for oxidant deactivation [Meister and Meister (1976) *Proc. Natl. Acad. Sci.* 78:420–422]. The small intestinal mucosa is a dynamic site of luminal protein breakdown and synthesis; GSH degradation may occur along the brush border allowing it to serve as an amino acid reservoir, especially for cysteine [Dahm and Jones (1994) *Am. J. Physiol* 267:G292–G300; Cho et al. (1981) *J. Nutr.* 111:914–922]. During limited nutrient supply, as in this study, GSH degradation by γ-glutamyl transpeptidases and dipeptidases at the apical surface of epithelial cells may increase as an adaptive mechanism to provide amino acids (cysteine, glycine and glutamate) for epithelial cell growth and function [Lash et al. (1986) *Proc. Natl. Acad. Sci.* 83:4641–4645; Martensson et al. (1989) *Proc. Natl. Acad. Sci.* 87:1715–1719; Meister and Meister (1976) supra].

Our data demonstrate a marked proximal to distal gradient for both GSH and the GSH redox potential. This gradient was not altered by level of refeeding or KGF administration. Dramatically greater GSH levels and antioxidant capacity in the colon indicate that a pronounced reducing environment exists in the distal region of the bowel during refeeding. GSH levels in the rat intestine during normal ad libitum feeding were previously reported to be similar throughout the small and large intestine [Ogasawara et al. (1989) *Res. Exp. Med.* 189:195–204; Seigers et al. (1988) *Cancer Lett.* 40:71–76]. It is possible that the differences in tissues distribution of GSH between these studies and our data are related to our model of refeeding after malnutrition-induced atrophy. The marked elevation in colonic GSH represents a tissue specific mechanism to protect the distal bowel from oxidant-mediated injury. In a study of endotoxin exposure in rats, GSH levels in colon were increased, but decreased in the duodenum and jejunum [Chen et al. (1988) *Biochem. Biophys. Res. Com.* 151:844–850]. Our current data indicate that the colon has the ability to increase antioxidant defenses in response to stresses including, but not limited to, malnutrition or starvation, especially when KGF is administered to the stressed animal or human.

Figure 4:
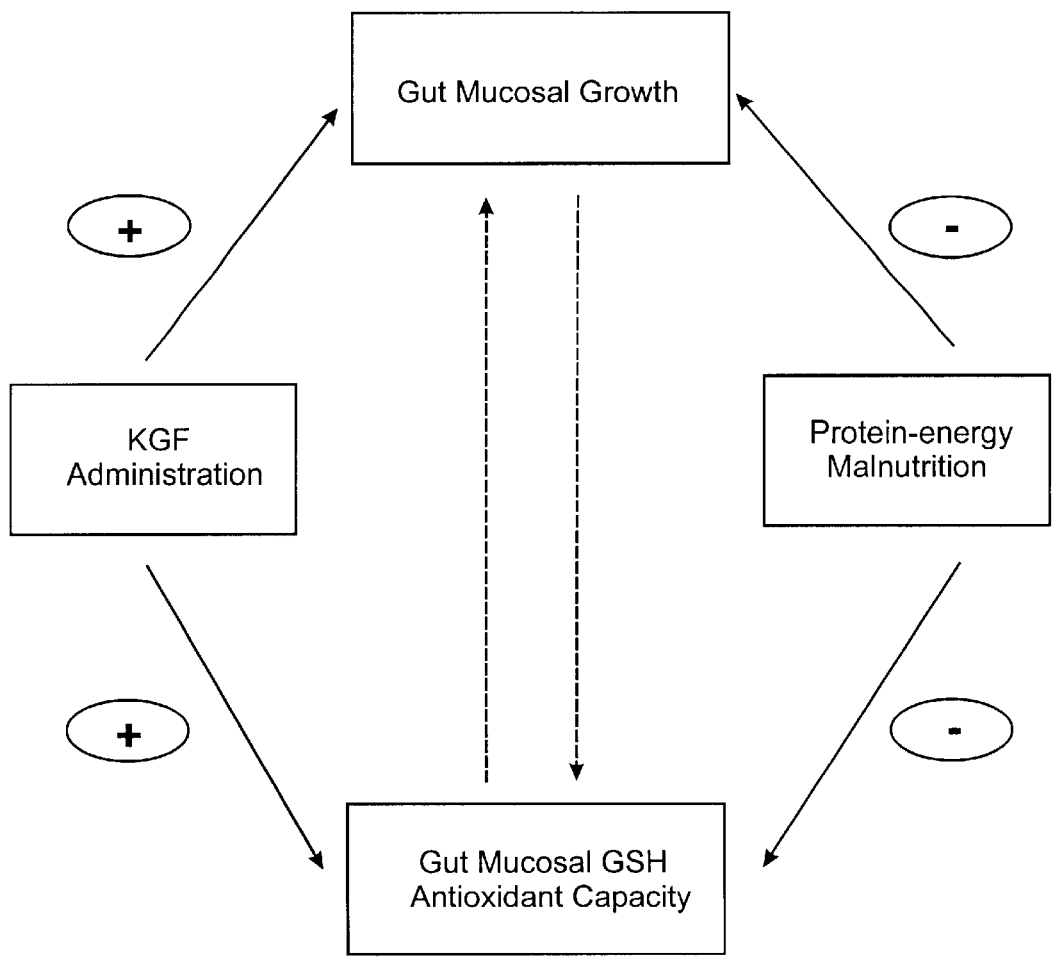
FIG. 4 provides a summary of KGF and nutrition effects on mucosal growth and GSH redox capacity.

In summary, in a rat model of fasting with different levels of enteral refeeding, the lower level of nutrient intake markedly decreased the glutathione content and resulted in a more oxidized glutathione redox potential in jejunal, ileal and colonic mucosa. The malnutrition-induced oxidation of the gut mucosal GSH pool was completely prevented by recombinant KGF administration during refeeding. The effects of KGF and nutritional status on mucosal growth and GSH status and their possible interactions are illustrated in FIG. 4. Increased intestinal antioxidant capacity observed after KGF administration indicates that this agent has a therapeutic role in malnutrition or other conditions associated with gut mucosal oxidative stress.

The effects of KGF administration on colonic mucosal GSH status and on mucosal protein oxidation during fasting were also studied. Adult rats were fasted for 3 days and given either intraperitoneal saline (FS) or KGF (3 mg/kg/day) (FK). Control rats were fed ad libitum and given saline (Control). GSH and glutathione disulfide (GSSG) in colonic mucosa were determined by HPLC, and the GSH redox potential (Eh) was calculated using the Nernst equation. Oxidatively modified proteins in mucosa were determined by a Western blot immunoassay, which detected 2,4-dinitrophenylhydrazine-derivatized protein carbonyl groups. Groups were compared by ANOVA and post-hoc fisher's PLSD test. Data are shown below (mean±SE).

| Group | GSH nmol/mg protein | GSH/GSSG | Eh (mV) |
| --- | --- | --- | --- |
| Fed Control | 27.5 ± 2.9 | 27.4 ± 2.6 | −227 ± 3 |
| FS | 15.4 ± 0.9* | 17.7 ± 08*† | −216 ± 1*† |
| FK | 18.4 ± 1.4 | 30.4 ± 2.4 | −226 ± 1 |

*$P < 0.01$ vs Control, †$P < 0.01$ vs FK: n = 8 per group

Fasting decreased GSH levels and oxidized the GSH pool in rat colonic mucosa. KGF treatment modestly increased mucosal GSH (NS), and completely prevented the decline in GSH/GSSG ratio and the loss of GSH reducing potential (Eh less negative). Total protein carbonyl content in colon was unchanged by fasting or KGF. KGF improves rat colonic mucosal GSH redox state in the absence of enteral nutrients. Colonic protein oxidation is not altered by fasting or KGF.

The following examples are provided for illustrative purposes, and are not intended to limit the scope of the invention as claimed herein. Any variations in the exemplified articles and/or methods which occur to the skilled artisan are intended to fall within the scope of the present invention.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning,* Second Edition, Cold Spring Harbor Laboratory, Plainview, N.Y.; Maniatis et al. (1982) *Molecular Cloning,* Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics,* Cold Spring Harbor Laboratory, Cold Spring Harbor, N.Y.; Old and Primrose (1981) *Principles of Gene Manipulation,* University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization,* IRL Press, Oxford, UK; and Setlow and Hollaender (1979) *Genetic Engineering: Principles and Methods,* Vols. 1–4, Plenum Press, New York. Abbreviations and nomenclature, where employed, are deemed standard in the field and commonly used in professional journals such as those cited herein.

All references cited in the present application are incorporated by reference herein to the extent that they are not inconsistent with the disclosure herein.

EXAMPLES

Example 1

Animals

Male Sprague-Dawley rats (Charles River Laboratories, MA) weighing 170–200 gm, were housed in individual cages in the animal care facility under controlled conditions of temperature and humidity with a 12-h light, 12-h dark cycle. Animals were enterally fed ad libitum water and standard pelleted rat food (Laboratory Rodent Chow 5001, PMI Feeds Inc., St. Louis, Mo.) during a 3 to 5 day acclimation period. The study protocol was approved by the Institutional Animal Use Committee of Emory University, Atlanta, Ga.

Example 2

Treatment Regimens

Rats were fasted for 3 days with ad libitum water to induce protein-energy malnutrition and intestinal mucosal atrophy [Ziegler et al. (1995) *Endocrinology* 136:5148–5154]. Weight-matched animals were the n assigned to one of four diet/KGF treatment regimens for 3 subsequent days: 1) ad libitum refeeding with daily saline (1 ml/day) intraperitoneal (i.p.) injection (A-SAL, n=8); 2) pair-refed to the ad libitum refed group intake with daily recombinant KGF injection (5 mg/kg/day, Amgen Inc., Thousand Oaks, Calif.) (A-KGF, n=6); 3) refed to 25% of the ad libitum intake with saline injection (25%-Sal, n=5); or 4) pair-refed to 25% of ad libitum intake with KGF injection (25%-KGF, n=5). The average daily food intake of the A-SAL group was determined during refeeding. This amount was provided to the A-KGF group daily and was used to calculate the daily 25%-refed group intakes. Actual food intake was monitored daily and all animals consumed their entire dietary ration. The study design is shown schematically in FIG. 1.

Example 3

Tissue Isolation

After the 72-hour refeeding period, animals were anesthetized with a ketamine (100 mg/ml) and xylazine (20 mg/ml) mixture administered intraperitoneally. The peritoneal cavity was opened by a midline incision and the ligament of Treitz was identified. The small and large bowel segments were stripped of mesenteric and vascular connections and sequentially removed from the peritoneum. The jejunal segment used for mucosal analysis was identified as the 4 cm portion from 10 to 14 cm distal to the ligament of Treitz, the ileum as the portion 10 to 14 cm proximal to the ileal-cecal junction, and the colon as the segment from 8 to 12 cm distal to the cecum. The lumen of each intestinal segment was flushed with 20–30 ml of ice-cold 0.9% NaCl to clear intestinal contents, and the segment was suspended from a ringstand with a constant distal weight. For histology studies, a defined 1 cm segment of intestine was excised. The segment used for mucosal GSH redox analysis was longitudinally cut, and the mucosa obtained by gentle scraping with a glass slide. The mucosa was immediately placed in a solution containing 5% perchloric acid, 0.2 M boric acid and 5 $\mu$M gamma-glutamylglutamate for HPLC analysis of thiols.

Example 4

Histology

The 1 cm segments of jejunum, ileum, and colon were cut longitudinally, fixed with formalin on gel foam, embedded in paraffin, and sectioned. Sections were stained with hematoxylin and eosin, and crypt depth and villus height measured using light microscopy for jejunum and ileum samples, and crypt depth only for colon samples. Measures were completed on 10 to 25 crypt and villi per tissue sample by two pathologists blinded to the treatment groups. Total mucosal height was calculated as the sum of crypt depth and villus height for jejunal and ileal samples and was utilized as an overall index of mucosal growth in the small intestine. Crypt depth represents the total mucosal height for the colon and was used as the index of mucosal growth for this tissue.

Example 5

GSH and GSSG Determination by HPLC

Mucosal samples were homogenized for 30 seconds and then sonicated for 15 sec at low setting. Precipitated tissue proteins were separated from the acid-soluble supernatant by microcentrifugation and the protein pellet was resuspended in 1 N NaOH. Protein concentrations were measured using the modified Bradford method and rabbit gamma-globulin as the protein standard (BioRad Laboratories, Hercules, Calif.). The acid-soluble supernatant was stored at −70° C. for 2 to 4 weeks until thiol analysis. At the time of analysis, GSH and GSSG contained in the acid-soluble fraction was derivatized with dansyl chloride using the method described by Jones et al. [Jones et al. (1995) *Immunol. Lett.* 45:205–209]. Briefly, 40 mM iodoacetic acid was added to the supernatant, followed by addition of 1 M KOH in saturated potassium tetraborate ($K_2B_4O_7$) to bring the sample pH to 9.0±0.2. After 20 min, dansyl chloride (20 mg/ml acetone) was added for dansyl derivatization of GSH and GSSG and incubated at room temperature in the dark for 24 h. Chloroform was then added to remove any unreacted dansyl chloride, and samples containing the chloroform and aqueous phases and the remaining precipitate phase were stored in the dark at −4° C. until analysis.

For HPLC separation, the samples were microcentrifuged for 2 min and an aliquot of the aqueous layer transferred to the HPLC autosampler. The dansyl-derivatized thiols, including GSH and GSSG, were separated on a 3-aminopropyl column (5 m; 4.6 mm×25 cm; Custom LC, Houston, Tex.) using a Waters 2690 HPLC and autosampler system (Waters, Milford, Mass.). For each sample, solvent conditions were run as described by Jones et al. [(1995) *Immunol. Lett.* 45:205–209]. Fluorescence detection of derivatives was obtained using bandpass filters set at 305–395 nm excitation and 510–650 nm emission (Gilson Medical Electronics, Middletown, Wis.). Quantitation of the thiols was calculated based on integration relative to the internal standard, gamma-glutamyl-glutamate, in each sample. Mucosal GSH and GSSG content was corrected for protein content and expressed as nmoles/mg protein.

Example 6

Calculation of GSH Redox State ($E_h$)

We calculated the reduction potential of the GSH/GSSG pool in intestinal and colonic mucosal samples using the Nernst equation (equation 1):

$$E_h = E_o + RT/2F \log[(GSSG)/(GSH)2] \quad [1]$$

The $E_h$ value obtained using this method provides a functional measure of the actual redox state of the tissue GSH pool as compared to expression of the ratio of reduced to oxidized GSH levels (GSH/GSSG). This is because the numerical value for the GSH/GSSG ratio under different conditions may be identical despite significant differences in actual tissue GSH and GSSG concentrations. The Nernst equation accounts for the stoichiometry of the GSH and GSSG reversible reaction (2 GSH to 1 GSSG). The derived value for $E_h$ is a function of the concentrations of both GSH and GSSG, and thus accurately expresses the ability of GSH to donate a hydrogen (or reduce an oxidant), as a function of the concentration of GSSG present. $E_h$ is expressed in units of millivolts and reflects the energy potential of GSH to act as a reductant within a given system.

The $E_o$ in equation 1 represents an electrode constant that is estimated for the GSH/GSSG redox couple (−0.24 V), and is pH-dependent [Rost and Rapaport (1964) *Nature* 201:185; Clarke, W. M. (1960) Waverly Press, Baltimore, pp. 248–272]. A pH effect of 59 mV/pH unit is expected for this biological system [Clarke, W. M. (1960) supra]. The pH of the intestinal and colonic mucosa has been previously reported as 7.3–7.4 [Wang et al. (1993) *Eur. J. Surg.* 159:81–87]. Thus, a value of $E_o$=−0.264 V was used for the $E_h$ calculations. For these data, the equation incorporated a temperature of 37° C. (T) for this system and the Faraday's constant (F, as 96,494 J/V/mol). The final equation used for these data is shown in equation 2.

$$E_h = -0.264 + 0.03 \log[(GSSG)/(GSH/2] \quad [2]$$

Example 7

Mucosal Growth and GSH Redox Indices

Data were obtained in this study to determine the relationship between indices of gut mucosal growth and gut mucosal GSH redox state in the study groups. We utilized previously determined histologic data on total mucosal height (crypt depth+villus height) from jejunum and ileum, and crypt depth from jejunum, ileum and colon. These indices were defined a priori as specific indices of gut mucosal growth.

Example 8

Statistical Analysis

The study was arranged as a 2×2 factorial design, with diet (ad libitum versus 25% of ad libitum) and treatment (KGF vs saline) as the main effects. Two-factor analysis of variance (ANOVA) was initially performed to determine the main effects of diet and KGF treatment and their interaction. One-factor ANOVA was utilized to detect significant inter-group differences (P<0.05). In this case, the four specific study groups were compared post-hoc using the Fisher's protected least-significant difference (PLSD) test.

One and two-way ANOVA were used to test the relationship between GSH levels, GSH redox state ($E_h$), and mucosal growth indices versus either group or diet and KGF (SAS; Cary, N.C.). These methods were used because diet and KGF administration are related to both GSH redox and mucosal growth parameters. Scattergrams were used to explore the associations between crypt depth versus GSH levels, crypt depth versus $E_h$ values, total mucosal height versus GSH levels, and total mucosal height versus $E_h$. One and two-way analysis of covariance (ANCOVA) were used to first test these linear associations while adjusting for group differences. Furthermore, group differences were tested while adjusting for linear associations.

TABLE 1

GSH and GSSG levels in jejunal, ileal, and *colonic mucosa.*

| | Jejunum | | Ileum | | Colon | |
| --- | --- | --- | --- | --- | --- | --- |
| | GSH (nmol/mg protein) | GSSG (nmol/mg protein) | GSH (nmol/mg protein) | GSSG (nmol/mg protein) | GSH (nmol/mg protein) | GSSG (nmol/mg protein) |
| A-Sal | 6.21 ± 0.45 | 0.81 ± 0.12 | 7.85 ± 0.67 | 0.56 ± 0.08 | 25.31 ± 3.47 | 1.59 ± 0.61 |
| A-KGF | 6.34 ± 0.30 | 0.52 ± 0.04[a] | 5.74 ± 0.67[a,f] | 0.24 ± 0.04[a] | 32.35 ± 6.50 | 0.47 ± 0.06[d] |
| 25%-Sal | 4.46 ± 0.81[a,b,f] | 0.69 ± 0.09 | 4.81 ± 0.90[a,f] | 0.87 ± 0.02[a,c,f] | 10.37 ± 2.33[a,e,c] | 0.90 ± 0.21[a] |
| 25%-KGF | 6.93 ± 0.44 | 0.57 ± 0.06 | 9.46 ± 0.88 | 0.37 ± 0.04 | 25.75 ± 3.24 | 0.92 ± 0.29[a] |

Values are means ± SEM. ([a]p < 0.05 vs. A-Sal; [b]p < 0.05 vs. A-KGF; [c]p < 0.05 vs. 25%-KGF, [d]p < 0.01 vs. A-Sal; [e]p < 0.01 vs. A-KGF; [f]p < 0.01 vs. 25%-KGF)

We claim:

1. A method for treating oxidative damage to the gastrointestinal tract in a human or an animal under a condition of malnutrition, fasting, undernutrition or during refeeding after said conditions, said method comprising the step of administering an effective amount of keratinocyte growth factor to said human or animal in need thereof.

2. The method of claim 1 wherein said keratinocyte growth factor is administered intraperitoneally.

3. The method of claim 1 wherein said keratinocyte growth factor is administered intravenously.

4. The method of claim 1 wherein said keratinocyte growth factor is administered parenterally.

5. The method of claim 1 wherein said keratinocyte growth factor is administered nonparenterally.

6. The method of claim 1 wherein said keratinocyte growth factor is administered in a dose from about 0.1 mg/kg body weight to about 5 mg/kg body weight.

7. The method of claim 6 wherein said keratinocyte growth factor is administered in a dose from about 0.5 mg/kg body weight to about 3 mg/kg body weight.

\* \* \* \* \*

UNITED STATES PATENT AND TRADEMARK OFFICE
CERTIFICATE OF CORRECTION

PATENT NO. : 6,228,839 B1
DATED : May 8, 2001
INVENTOR(S) : Zielger et al.

It is certified that error appears in the above-identified patent and that said Letters Patent is hereby corrected as shown below:

Column 1,
Line 27, replace "result" with -- results --.

Column 4,
Line 9, "EP 619,271" with -- EP 619,370 --.
Line 23, replace "pharmaceutically" with -- pharmaceutical --.

Column 11,
Line 23, delete "the n".

Signed and Sealed this

Eighteenth Day of December, 2001

Attest:

JAMES E. ROGAN
Attesting Officer
Director of the United States Patent and Trademark Office